United States Patent
Williams et al.

(10) Patent No.: US 6,203,320 B1
(45) Date of Patent: Mar. 20, 2001

(54) ELECTRIC TOOTHBRUSH AND METHOD COMBINING BRISTLE AND PULSED LIQUID IRRIGATION CLEANSING TO ORAL CAVITY

(75) Inventors: David Robert Williams, Monroe; Richard Steven Hart, Naugatuck, both of CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/291,218

(22) Filed: Apr. 14, 1999

Related U.S. Application Data
(60) Provisional application No. 60/113,289, filed on Dec. 22, 1998.

(51) Int. Cl.[7] .............................. A61G 17/02; A61C 1/10; A45D 44/18; A46B 9/04
(52) U.S. Cl. .................. 433/80; 433/82; 132/308; 15/167.1
(58) Field of Search ................. 433/80, 82, 84, 433/85, 86; 15/22.1, 167.1; 601/162, 163, 164, 165; 132/308, 310

(56) References Cited

U.S. PATENT DOCUMENTS

| | | | |
|---|---|---|---|
| 4,279,053 | 7/1981 | Payne et al. ............................ | 15/159 |
| 4,429,434 | 2/1984 | Sung-shan ............................. | 15/341 |
| 4,580,588 | * 4/1986 | Swope ................................. | 132/308 |
| 4,672,953 | * 6/1987 | Divito ................................. | 433/80 |
| 4,743,199 | * 5/1988 | Weber et al. ........................... | 433/80 |
| 5,029,576 | * 7/1991 | Evans ................................. | 433/80 |
| 5,056,480 | 10/1991 | Murray, Sr. ........................... | 132/124 |
| 5,098,291 | * 3/1992 | Curtis et al. ........................... | 433/80 |
| 5,150,492 | 9/1992 | Suroff ................................. | 15/22.1 |
| 5,208,933 | 5/1993 | Lustig et al. ........................... | 15/22.1 |
| 5,246,301 | 9/1993 | Hirasawa .............................. | 401/28 |
| 5,286,192 | * 2/1994 | Dixon ................................. | 433/80 |
| 5,309,590 | * 5/1994 | Giuliani et al. ......................... | 15/22.1 |
| 5,321,865 | 6/1994 | Kaeser ................................ | 15/22.1 |
| 5,344,317 | * 9/1994 | Pacher et al. .......................... | 433/80 |
| 5,561,881 | 10/1996 | Klinger et al. .......................... | 15/22.1 |
| 5,573,398 | 11/1996 | Towle et al. ........................... | 433/80 |
| 5,625,916 | 5/1997 | McDougall ........................... | 15/28 |
| 5,640,735 | 6/1997 | Manning .............................. | 15/29 |
| 5,651,157 | 7/1997 | Hahn ................................. | 15/22.1 |
| 5,653,591 | * 8/1997 | Loge ................................. | 433/18 |
| 5,658,148 | * 8/1997 | Neuberger et al. ..................... | 433/215 |
| 5,669,097 | 9/1997 | Klinkhammer ........................ | 15/167.1 |
| 5,746,595 | * 5/1998 | Ford .................................. | 433/80 |
| 5,820,373 | * 10/1998 | Okano et al. .......................... | 433/80 |
| 5,836,769 | * 11/1998 | Spencer .............................. | 433/216 |
| 5,928,505 | * 6/1999 | Inakagata et al. ...................... | 433/80 |
| 5,933,906 | * 8/1999 | Racklley .............................. | 15/167.1 |

* cited by examiner

*Primary Examiner*—John J. Wilson
*Assistant Examiner*—Robyn Kieu Doan
(74) *Attorney, Agent, or Firm*—Milton L. Honig

(57) ABSTRACT

An electrically operated toothbrush and method for cleaning teeth and stimulating gums is provided. The toothbrush includes a handle, a brushhead connected to the handle having a plurality of hollow filament bristles, passageways through the handle and brushhead for transporting fluid such as water into and through the hollow filament bristles, an electrical energy source in the handle and a vibratory element for imparting a pulsation to the fluid being transported.

6 Claims, 1 Drawing Sheet

Figure 1:
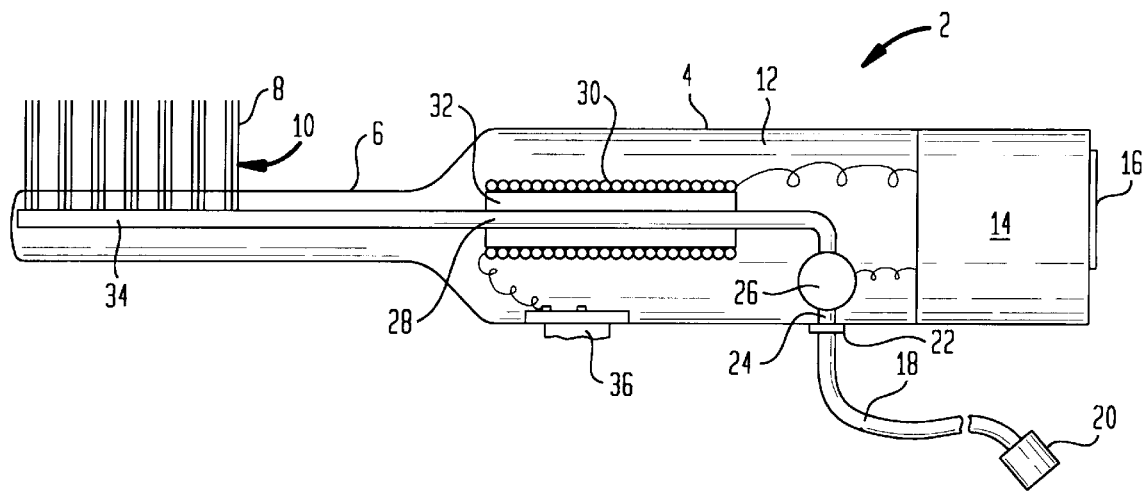

ELECTRIC TOOTHBRUSH AND METHOD COMBINING BRISTLE AND PULSED LIQUID IRRIGATION CLEANSING TO ORAL CAVITY

This application claims benefit to provisional application 60/113,289 filed Dec. 22, 1998.

BACKGROUND OF THE INVENTION

1. Field of the Invention

The invention concerns an electric toothbrush combining the oral cavity cleansing benefits of bristles and liquid irrigation. The efficiency of power brush cleaning is united with pulsed water to effectively remove plaque from tooth surfaces and to stimulate the gums.

2. The Related Art

It has been established that significant benefits are derived from regular dental care performed in the home by the individual himself together with periodic examination and treatment by professionally trained dentists. It is universally recognized, for example, that regular brushing of the teeth, particularly after every meal, serves to dislodge food particles which ordinarily are retained adjacent the teeth and which, if allowed to remain, would cause decay and dental caries. When properly administered, regular brushing also serves to maintain good circulation in gingival tissue, thereby lessening the likelihood of gingival disease, one of the prime causes of premature loss of teeth. Perhaps of less, but nevertheless significant, importance are the stain removal and brightening actions resulting from regular brushing, which contribute noticeably to the appearance of the individual.

Mechanized toothbrush systems are particularly popular for this purpose. Generally they involve rapid movement of bristles operated by a suitable power source. Power may be imparted through a water driven turbine or an electrically driven mechanism involving a set of gears. More recently ultrasonic vibrational energy has been employed.

U.S. Pat. No. 5,150,492 (Suroff) reports that ultrasonic energy when applied under proper control to tooth and gingival surfaces in the human mouth may successfully be employed for regular oral hygienic care without any damage to tooth surfaces or gingival tissues. Ultrasonic cleaning techniques were said to provide a significantly increased cleaning ability around the interproximal and gum line areas in contrast to the inadequate brushing techniques of prior commercial toothbrushes. This patent teaches coupling the toothbrush to a power means and transferring ultrasonic energy from the power means to the ultrasonic implement with the former remaining substantially free from absorbing ultrasonic energy as the vibratory energy is transmitted.

U.S. Pat. No. 5,321,865 (Kaeser et al.) combines the features of a motorized back and forth motion of the brush and use of a pulsating stream of highly pressurized water for final rinsing of the teeth with massaging of the gums.

While mechanized toothbrush technology has significantly advanced, there is still a need for further improvement.

Accordingly, it is an object of the present invention to provide an electric toothbrush that combines the efficiency of power brush cleaning with pulsed irrigation to effectively remove plaque from all tooth surfaces.

This and other objects of the present invention will become more readily apparent through consideration of the following summary and detailed discussion.

SUMMARY OF THE INVENTION

An electronically operated toothbrush is provided which includes:

(i) a handle;

(ii) a brushhead connected to the handle, the brushhead having a plurality of hollow filament bristles;

(iii) at least one passageway through the handle and brushhead for transporting fluid into and through the hollow filament bristles;

(iv) a source of electrical energy attached to the handle; and (v) a vibrational element activated by the source of electrical energy, the vibrational element imparting a pulsation to the fluid being transported to the hollow filament bristles.

Useful for the present invention are hollow filament bristles having either a circular or a non-circular cross-section. Preferably the void content of the filaments may range from about 20 to about 70%. A most preferred form of pulsation is that of an ultrasonic wave pulse pattern.

Another aspect of the present invention is a method for cleaning teeth and stimulating gums which includes:

(i) providing a toothbrush having a brushhead fitted with a plurality of hollow filament bristles;

(ii) feeding tooth irrigating fluid into the toothbrush;

(iii) imparting a pulsation to the fluid which is then transported through the hollow filament bristles; and (iv) contacting teeth and gums in an oral cavity with the pulsating fluid to remove oral debris.

DETAILED DESCRIPTION OF THE DRAWING

Figure 2:
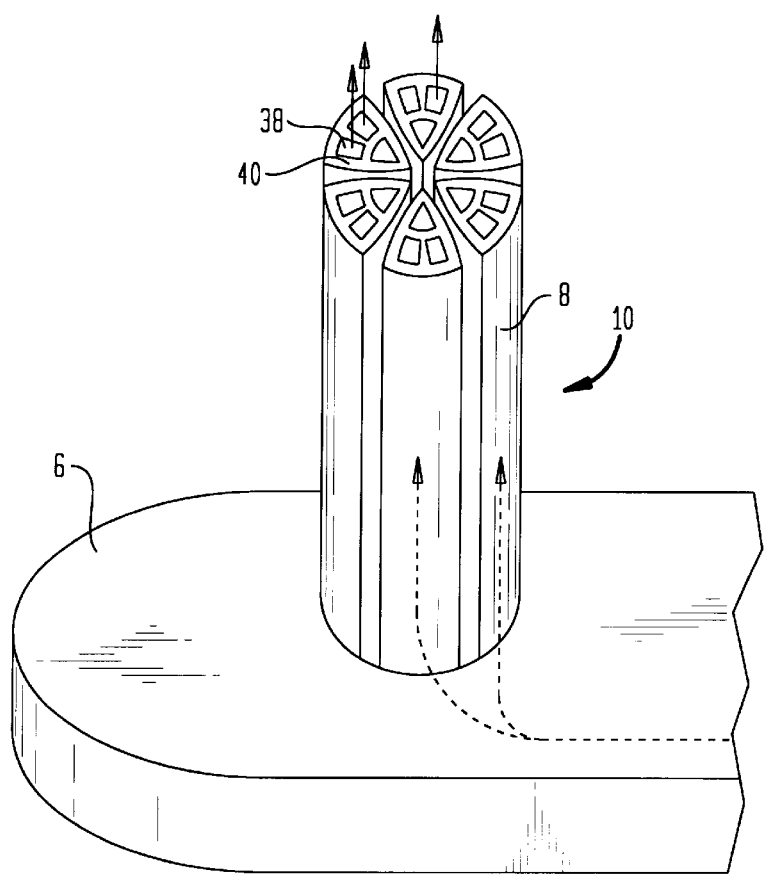

The various objects, features and advantages of the present invention will be better understood with reference to an exemplary embodiment illustrated in the drawing wherein:

FIG. 1 is a highly schematic cross-sectional view of an electrical toothbrush according to the present invention; and FIG. 2 is a highly schematic expanded partial view of the brushhead showing a bundle of hollow filament bristles.

DETAILED DESCRIPTION OF THE INVENTION

An electric toothbrush is described which combines the oral cavity cleansing benefits of a brush and of pulsed fluid irrigation. Plaque and other debris can be effectively removed from all tooth surfaces. Bristles of the brush are hollow to allow for flow-through of irrigating liquid. The irrigating liquid can be any fluid with flow properties similar to water. Pulsing can be done at any frequency range which maximizes stimulation and plaque removal. Preferably the frequency will be that of ultrasound to enable additional ultrasonic cleaning. Unlike the known art, delivery of a pulsating wave such as ultrasound is imparted to the irrigating liquid rather than to the bristles. A problem with pulsating the bristles is that upon contact with the teeth movement of the bristles is dampened. Pulsating liquid flow is much less effected by the dampening effect.

FIG. 1 provides a highly schematic cross-sectional diagram of an electric toothbrush according to the present invention. The toothbrush 2 in its major structural parts consists of a handle 4 and a brushhead 6. Bristles 8 are mounted onto the brushhead in tuft groups 10. Each tuft group may contain anywhere from about 2 to about 300 bristles. Total number of tuft groups may range from about 2 to about 100, preferably from about 10 to about 70.

Housing 12 defines the handle 4. Within the housing is an electrical energy supply source 14. Typically batteries may be employed as the source of electrical energy. Particularly preferred are rechargeable batteries which can be re-energized by inserting the toothbrush via its electrical coupling port 16 to a battery recharging stand.

Irrigation fluid may be supplied to the housing via an exterior conduit 18. One end of the conduit 18 has a water coupling 20 for attachment to a faucet. The other end of exterior conduit 18 is attached to a housing coupling 22 which transmits fluid along a passageway 24 into a pump 26.

Alternatively, the irrigation fluid may be held in a reservoir totally within housing 12. Pump 26 is electrically powered by the energy supply source 14 and functions to promote movement of fluid (e.g. by pressurization). As fluid exits the pump, it flows through interior conduit 28.

Many different types of pumps may be suitable for the present invention. Peristaltic pumps are one variety. Another type is described in U.S. Pat. No. 5,321,865. The pump itself may be the source of vibrational pulsing when lower frequencies are desired. For higher frequencies, the pump can be coupled with a variety of pulsation or oscillator devices known in the general art. Of particular advantage for the present invention are ultrasonic oscillators, particularly those operating within the range from about 10 to about 100,000, preferably from about 20,000 to about 50,000 Hz per second. In one embodiment shown in FIG. 1, an energy source 14 delivers power through an electrical conductive coil 30 which generates an alternating driving magnetic field. Coil 30 surrounds a vibrating element 32 such as a ferrite. When a magnetic field is generated through coil 30, a significant elongation of the vibrating element 32 will occur. The vibrating element will be of a length substantially equal to an integral number of quarter wavelengths corresponding to the driving magnetic frequency. Maximum conversion of energy is thereby achieved from the magnetic field to the mechanical vibration. The aforementioned vibrating material is normally a ferrite. Other forms of electrical to mechanical transducers may also be utilized such as piezoelectric and magneto restrictive devices.

Fluid passing through interior conduit 28 will receive pulsation energy from the vibratory element 32. The pulsating fluid will then enter brushhead conduits 34 and flow outwards through the hollow interiors of filaments forming bristles 8. A control knob 36 operates the electrical connection within the toothbrush. Water is normally the fluid of choice. Additives may be added to the water including flavorants (e.g. menthol, methyl salicylate, anethole etc.), preservatives, colorants, fluorides, ethanol, bacteriostats (e.g. triclosan, zinc salts, and quaternary ammonium compounds) and mixtures thereof.

Hollow bristles of the present invention may have a circular or non-circular cross-section. See FIG. 2. These filaments will in their longitudinal direction have multiple voids 38, particularly three or four voids. These voids are separated by internal web 40 and in cross-section may have trilocular, tetralocular, rectangular, hexagonal, circular or other polygonal cross-sections as well as combinations thereof. Preferred embodiments have cross-sectional dimensions ranging from about 4 to about 20 mils. Void content of filaments are from about 20 to about 70%. Suitable materials are thermoplastic polymers such as polyamides, polyesters and polyolefins. Most preferred are nylon 66, nylon 610 and nylon 612. These hollow filaments are commercially available from the Dupont Company.

Free ends of the bristles may be obliquely cut to provide an angular cross-section which may have advantages in delivering pulsating irrigating fluid to teeth and gums.

Except in the operating and comparative examples, or where otherwise explicitly indicated, all numbers in this description indicating amounts of material ought to be understood as modified by the word "about".

The foregoing description and examples illustrate selected embodiments of the present invention. In light thereof variations and modifications will be suggested to one skilled in the art, all of which are within the spirit and purview of this invention.

What is claimed is:

1. An electronically operated toothbrush comprising:
   (i) a handle;
   (ii) a brushhead connected to the handle, the brushhead having a plurality of non-circular cross-section hollow filament bristles;
   (iii) at least one passageway through the handle and brushhead for transporting water into and through the hollow filament bristles;
   (iv) a source of electrical energy attached to the handle; and
   (v) a vibrational element activated by the source of electric energy, the vibrational element imparting an ultrasonic wave pulsation to the water being transported to the hollow filament bristles.

2. The toothbrush according to claim 1 wherein the hollow filament bristles have a void content from about 20 to about 70%.

3. The toothbrush according to claim 1 wherein the electrical energy source is a battery lodged within the handle.

4. The toothbrush according to claim 1 further comprising a pump activated by the source of electrical energy for pumping water to the hollow filament bristles.

5. A method for cleaning teeth and stimulating gums comprising:
   (i) providing a toothbrush having a brushhead fitted with a plurality of non-circular cross-section hollow filament bristles;
   (ii) feeding tooth irrigating water into the toothbrush;
   (iii) imparting an ultrasonic wave pulsation to the water which is then transported through the hollow filament bristles; and
   (iv) contacting teeth and gums in an oral cavity with the pulsating water to remove oral debris.

6. The method according to claim 5 wherein the hollow filament bristles have a void content from about 20 to about 70%.

* * * * *